United States Patent
Pusterla et al.

(10) Patent No.: US 6,895,339 B2
(45) Date of Patent: May 17, 2005

(54) METHOD FOR MEASURING THE CONCENTRATION OF WATER IN ARGON, HYDROGEN, NITROGEN AND HELIUM BY IONIZATION MOBILITY SPECTROMETRY

(75) Inventors: Luca Pusterla, Milan (IT); Antonio Bonucci, Milan (IT); Marco Succi, Milan (IT); Robert Stimac, Palm Beach Gardens, FL (US)

(73) Assignee: Saes Getters S.p.A, Lainate (IT)

( * ) Notice: Subject to any disclaimer, the term of this patent is extended or adjusted under 35 U.S.C. 154(b) by 0 days.

(21) Appl. No.: 10/722,190

(22) Filed: Nov. 25, 2003

(65) Prior Publication Data

US 2004/0111222 A1 Jun. 10, 2004

Related U.S. Application Data

(63) Continuation of application No. PCT/IT02/00370, filed on Jun. 6, 2002.

(30) Foreign Application Priority Data

Jun. 6, 2001 (IT) ..................................... MI2001A1193

(51) Int. Cl.[7] .............................................. B01D 59/44
(52) U.S. Cl. ............................. 702/24; 702/23; 702/32; 250/282; 250/283
(58) Field of Search ............................. 702/21, 23, 24, 702/27, 30–32, 66, 70, 71, 73, 76, 78, 79, 85, 129, 176, 178, 189; 250/281–283, 286, 287, 252.1, 339.07, 339.09; 700/266; 436/52, 103, 171, 153; 422/89, 83; 73/23.2, 23.21, 23.22, 23.33, 23.35–23.37

(56) References Cited

U.S. PATENT DOCUMENTS

| 4,551,624 A | 11/1985 | Spangler et al. | 250/287 |
| 5,032,721 A | 7/1991 | Bacon et al. | 250/282 |
| 5,095,206 A | 3/1992 | Bacon et al. | 250/282 |
| 5,238,199 A | 8/1993 | Ossoinig et al. | 242/361.4 |
| 5,457,316 A | 10/1995 | Cohen et al. | 250/286 |
| 5,556,603 A | 9/1996 | Succi et al. | 422/213 |
| 5,558,844 A | 9/1996 | Succi et al. | 423/230 |
| 5,955,886 A | 9/1999 | Cohen et al. | 324/464 |
| 6,291,821 B1 * | 9/2001 | Danylewych-May et al. | 250/286 |
| 6,498,342 B1 * | 12/2002 | Clemmer | 250/287 |
| 6,509,562 B1 * | 1/2003 | Yang et al. | 250/287 |

FOREIGN PATENT DOCUMENTS

| GB | 2 177 079 A | 1/1987 |
| GB | 2 177 080 A | 1/1987 |

OTHER PUBLICATIONS

Stimac et al., "Water Vapor Measurements In Small Volumes Using Atmospheric Pressure Chemical Ionization—Mass Spectrometry", *Proceedings of the Annual Symposium On Reliability Physics.*, vol. Proc. 20, pp. 260–263, (1982), (no month).

Stimac et al., "Use Of Ion Mobility Spectrometry To Determine Trace Level Impurities In Ultra High Purity Gases" *proceedings Institute Of Environmental Sciences*, pp. 5–12, (1996), (no month).

* cited by examiner

*Primary Examiner*—Hal Wachsman
(74) *Attorney, Agent, or Firm*—Akin Gump Strauss Hauer & Feld, LLP

(57) ABSTRACT

A method is provided for measuring by ionization mobility spectrometry (IMS) relatively high concentrations of water in argon, hydrogen, nitrogen and/or helium, including the following steps: (a) introducing the gas to be analyzed into an IMS instrument with a counter-flow of pure gas; (b) obtaining a signal variable over time and proportional to the number of ions detected by an ion detector of the IMS instrument; (c) determining two time intervals (A, B) corresponding to the drift times in the IMS instrument of the $H_3O^+$ and $(H_2O)_2^+$ ions; (d) obtaining the peaks of the signal in the two determined time intervals (A, B); and (e) calculating the water concentration in the gas to be analyzed according to the ratio between the intensity of the two peaks obtained in the signal.

8 Claims, 3 Drawing Sheets

Introducing a gas mixture to be analyzed comprising water and at least one selected from the group consisting of argon, hydrogen, nitrogen, and helium into an IMS instrument with a counter-flow of pure gas Obtaining a signal variable over time and proportional to a number of ions detected by an ion detector of the IMS instrument Determining two time intervals (A, B) corresponding to drift times in the IMS instrument of $H_3O^+$ and $(H_2O)_2^+$ ions present in the gas mixture Obtaining peaks of the signal in the two determined time intervals (A, B)

Calculating the water concentration in the gas mixture according to a ratio of intensity of the two peaks obtained in the signal.

*Fig. 4*

METHOD FOR MEASURING THE CONCENTRATION OF WATER IN ARGON, HYDROGEN, NITROGEN AND HELIUM BY IONIZATION MOBILITY SPECTROMETRY

CROSS-REFERENCE TO RELATED APPLICATIONS

This application is a continuation of International Application No. PCT/IT02/00370, filed Jun. 6, 2002, which was published in the English language on Dec. 12, 2002, under International Publication No. WO 02/099405 A2.

BACKGROUND OF THE INVENTION

The present invention relates to a method for measuring the concentration of water in argon, hydrogen, nitrogen and helium by ionization mobility spectrometry.

These gases are widely used in the semiconductor industry as transport gases in which reactive species are diluted or as support gases for plasma formation in cathodic deposition processes (in particular, helium and argon are employed for these uses), as well as real reagents in the process (in particular in the case of nitrogen). Among these gases, argon is the most important for industry. In the rest of this specification this gas will be mainly referred to, but the invention may also be applied with the same results to the other cited gases.

The pureness of the argon employed in the semiconductor industry is particularly important. As a matter of fact, contaminants which may he present in the reagents or in the reaction environment can be incorporated into the solid state devices, thereby altering their electrical or magnetic properties and thus leading to production rejects.

Argon purification is the subject-matter of various patents, such as British Patent GB-B2177079 (similarly, British Patent GB-B-2177080 relates to nitrogen purification and U.S. Pat. Nos. 5,558,844 and 5,556,603 relate to hydrogen purification). According to this patent, argon is purified by passing it through a bed made of a getter material (an alloy based on zirconium, vanadium and iron) kept at a temperature between 350 and 450° C. Alternatively, purifiers working at room temperature are commonly employed, which are based on the use of nickel generally dispersed onto a high surface area support, such as alumina or molecular sieves. With these methods the impurity content can be reduced below one part per billion (ppb, equivalent to one impurity molecule for every $10^9$ molecules of argon).

Under these conditions it is also necessary to allow for control of the gas purity and its constancy over time, for detecting increments of the impurity concentration, due for example to working anomalies of the purifiers, tightness losses of the gas lines or other reasons.

A particularly interesting technique for carrying out this analysis is ionization mobility spectrometry, also referred to in the field with the initials IMS (the same initials are also used for the instrument carrying out this technique, i.e., "Ionization Mobility Spectrometer"). Interest in this technique derives from its very high sensitivity, combined with the limited size and costs of the instrument. By operating under suitable conditions species in the gas or vapor phase can be detected in a gas medium in quantities of picograms (pg, i.e., $10^{-12}$ grams), or in concentrations of parts per trillion (ppt, equivalent to a molecule of the analyzed substance for every $10^{12}$ molecules of the gas sample). IMS instruments and analysis methods in which these are employed are disclosed, for example, in U.S. Pat. Nos. 5,457,316 and 5,955,886 in the name of the US company PCP Inc.

An IMS instrument is essentially made up of a reaction zone, a separation zone and a charged particles detector.

In the reaction zone the ionization of the sample comprising the gases or vapors to be analyzed in a transport gas takes place, commonly by means of beta-radiation emitted by $^{63}Ni$. The ionization takes place mainly on the transport gas with the formation of the so-called "reagent ions," whose charge is then distributed on the species present according to their electronic or proton affinities or to their ionization potentials. The book "Ion Mobility Spectrometry" by G. A. Eiceman and Z. Karpas, published in 1994 by CRC Press, can be referred to for an illustration of the (rather complex) charge transfer principles which are the basis of the ionization mobility spectrometry technique.

The reaction zone is divided from the separation zone by a grid which, kept at a suitable voltage, prevents the ions produced in the reaction zone from entering into the separation zone. The moment at which the grid voltage is turned off, thus allowing the ions to enter the separation zone, is the "time zero" of the analysis. The separation zone comprises a series of electrodes, which create an electric field such that the ions are carried from the reaction zone toward the detector. This zone is kept at atmospheric pressure. Therefore, the motion speed of the ions depends on the electric field and on the cross-section thereof in the gaseous medium. By recording the current reading of the particle detector according to the time elapsed from "time zero," peaks corresponding to the so-called "drift time" of the different present ions are obtained. By determining the drift time it is possible to go back to the presence of the substances which are the object of the analysis.

In spite of its conceptual simplicity, the application of the technique involves some difficulties in the interpretation of the analysis results.

The instrument, analogously to chromatographs, provides as a result of the analysis the crossing times (drift times in the case of the IMS) of the ions corresponding to the species present, but it does not provide indications about the chemical nature of the ion corresponding to each peak.

For attributing each peak to a specific ion, the IMS may be connected to a mass spectrometer, which determines the chemical nature of each ion, but in this way the above mentioned advantages of low cost and compactness are renounced.

Alternatively, it is possible to resort to calibration tests, wherein a sample formed of an extremely pure transport gas containing the substance which is the object of the analysis is used, and the drift time of this latter gas is determined. However, the analysis under real conditions is complicated, since the various ionic species which are present may lead to phenomena of charge transfer with each other or with neutral molecules present, so that the determined drift times can be the characteristic times of species different from those whose presence is to be determined.

A possible method for overcoming the problems found in the real analyses consists in adding the sample gas with a specific substance, called a "doping gas," which, according to various mechanisms, obtains the effect of significantly decreasing the sensitivity of the measurement toward the species differing from the one which is the object of the analysis. As examples of practical application of the method of the doping gas may be mentioned U.S. Pat. No. 4,551,624, relating to the addition of ketones or halogenated gases to the gas to be analyzed; U.S. Pat. Nos. 5,032,721 and 5,095,206, relating, respectively, to the use of phenols and sulfur dioxide in the analysis of acid gases; and U.S. Pat. No.

5,238,199, relating to the use of amines in the analysis of chlorine dioxide. However, the doping gas method disadvantageously requires that a tank of this gas and means for its dosage in the gaseous medium are added to the system, thus leading to a complication of the measuring system based on the IMS instrument.

In the methods not based on the employment of a doping gas the possibility of carrying out a quantitative analysis is bound to the presence of a reactant ion. As previously described, the reactant ion generally is an ion corresponding to the gas present in higher amount in the mixture. Then, the reactant ion formed in the ionization zone transfers the charge to the other species present according to complex chemical balances. When the concentration of impurities increases, the charge quantity transferred thereto from the reactant ion also increases, until the latter is extinguished. In the IMS spectrum this mechanism is reflected by the intensity increase of the peaks related to the impurities and by the simultaneous intensity decrease of the peak of the reactant ion, commonly defined in the field as "Reactant Ion Peak" or RIP, up to its extinction. Obviously, when this condition is reached, the concentration of the ions relating to the impurities and the intensity of the relevant peaks in the spectrum do not grow any more, even if the effective impurity concentration increases and therefore it is no longer possible to carry out a quantitative IMS analysis in this way. In the presence of water in argon, the RIP is extinguished with concentrations of about 10–15 ppb. Thus, according to the state of the art, this value is the maximum measurement limit of this impurity in argon with the IMS technique.

BRIEF SUMMARY OF THE INVENTION

It is therefore an object of the present invention to provide a method which is free from these disadvantages, i.e., a method allowing the measurement of water concentrations greater than 15 ppb. This object is achieved by a method for measuring the concentration of water in argon, hydrogen, nitrogen and helium by ionization mobility spectrometry (IMS), comprising the followings operative steps:

introducing a gas mixture to be analyzed into an IMS instrument with a counter-flow of pure gas;

obtaining a signal variable over time and proportional to a number of ions detected by an ion detector of the IMS instrument;

determining two time intervals (A, B) corresponding to drift times in the IMS instrument of $H_3O^+$ and $(H_2O)_2^+$ ions present in the gas mixture;

obtaining peaks of the signal in the two determined time intervals (A, B); and calculating the water concentration in the gas mixture according to a ratio of intensity of the two peaks obtained in the signal. Other features of the method are disclosed below.

Thanks to the calculation of the ratio between the intensities of the peaks detected at determined time positions in the signal coming from an IMS instrument, the method according to the present invention allows precise measurement of water concentrations in argon up to at least 30 ppb. The measurement of the peak intensity in practice generally consists in the measurement of their area.

Furthermore, the method according to the present invention, when applied to the ultra-pure argon employed in the semiconductor industry (such as hydrogen, nitrogen and helium), does not require either doping gases or gas purification processes before the IMS analysis, except when the same gas has impurities in relatively high concentrations, generally greater than about 10 ppb for each impurity.

According to a particular aspect of the invention, the calculation of the water concentration can be carried out in an automatic manner by using a logarithmic formula which can be easily implemented in an electronic calculator, for instance in a personal computer.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 4 is a flow chart depicting the method according to the invention.

DETAILED DESCRIPTION OF THE INVENTION

Figure 1:
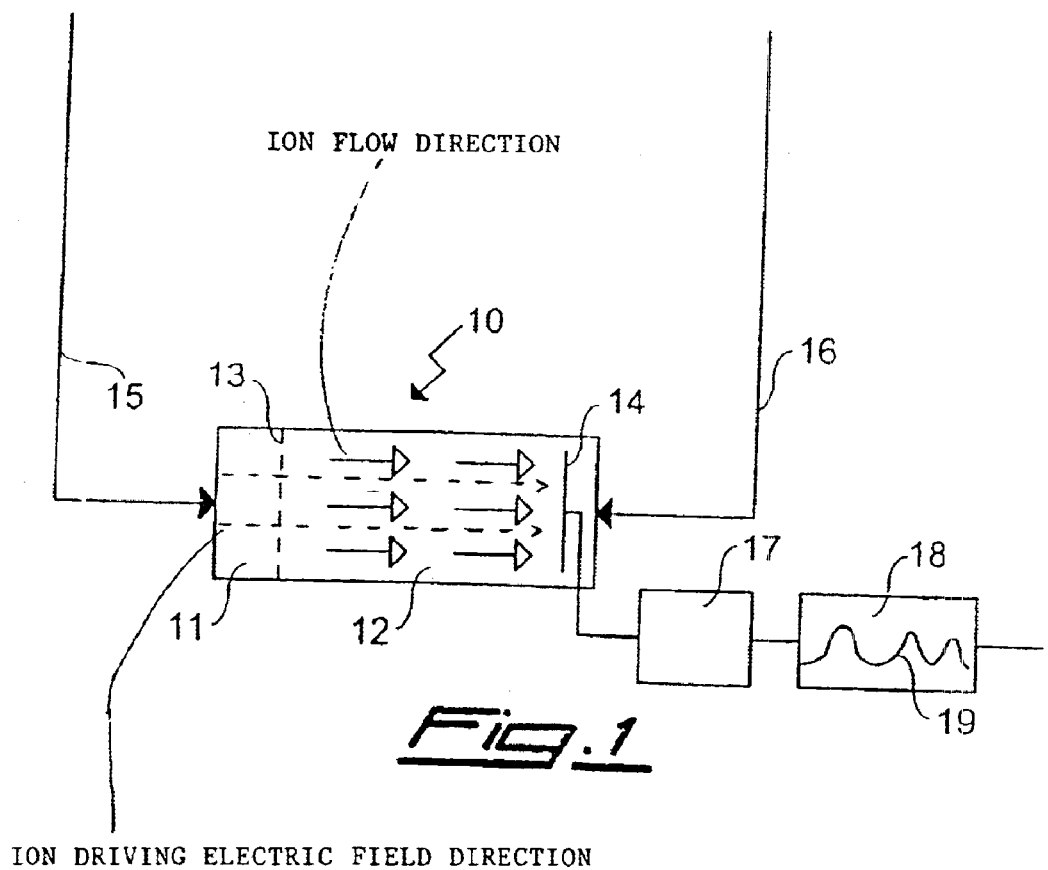
FIG. 1 is a schematic diagram of an instrument for carrying out the method according to the present invention.

Referring to FIG. 1, it is seen that an IMS instrument 10 comprises in a known way a reaction zone 11 and a separation zone 12, which are divided by a grid 13. The gases let into the reaction zone 11 are ionized by a radiation source (not shown in the Fig.), for instance $^{63}$Ni. The so produced ions are guided into the separation zone 12 where, by electrodes (not shown in the Fig.) suitably arranged along the walls of this zone, the ions are accelerated toward an ion detector 14. The ions motion in the separation zone 12 is schematically represented in FIG. 1 by the arrows. The gas to be analyzed is let into the IMS instrument 10 through an inlet duct 15. The motion speed toward the ion detector 14 is slowed down by the presence of a counter-current flow of pure argon in the zone 12. For this purpose the IMS instrument 10 comprises at least one duct 16 for introducing argon into the separation zone 12 from the side of detector 14. The detector 14 is connected to a converter 17, which transforms the progress over time of the electric signal of detector 14 into an analog or digital signal, which in turn can be displayed on a display and/or a printer 18 by a spectrum 19 representing the result of the analysis.

Ducts 15 and 16 are preferably manufactured according to the usual techniques of pure gas technology, which generally involve the use of electro-polished steel pipes for ensuring extremely limited degassing from the internal walls of these ducts.

According to the invention, the gas to be analyzed is introduced into the reaction zone 11 of the IMS instrument 10 and analyzed according to the typical way of this technique, i.e., by employing in the separation zone 12 of the IMS instrument 10 a counter-flow of a gas which does not interfere with the measurement, in particular argon. As will be described in detail later on, the position in the spectrum (in milliseconds, ms) of the peak due to argon, i.e., of the RIP, is known by knowledge of the test parameters. When the measuring system detects the RIP extinction, two peaks corresponding to two different ionic species relating to water are sought. By comparing the intensities of these two peaks, the water concentration in argon is calculated, in particular by means of a logarithmic formula.

The position of the RIP, as well as any other peak in an IMS spectrum, depends on the physical parameters with which the analysis is carried out. In particular, the most important parameter is the temperature of the gas in the separation zone. Thus, considerable temperature changes with respect to a reference temperature may change the ratios between the time position of various peaks in the spectrum, thereby making the analysis impossible. A second important parameter is the ratio between the applied electric field and the gas pressure in the separation zone. Changes of this ratio cause proportional changes of the positions of all the peaks in the spectrum, so that the spectrum is "compressed" or "expanded," although the ratios between the various peak positions are maintained. Anyway, for convenience, it is preferable that the drift times remain fixed, for facilitating the identification of the different peaks. Finally, the spectrum is influenced by the ratio between the mass flow of gas to be analyzed and the mass flow of the counter-current gas, though to a lesser extent than the previous parameters. The two peaks relating to water, which are important for the method according to the invention, are the peaks corresponding to $H_3O^+$ and $(H_2O)_2^+$ ions. Therefore, to know the time position of these two peaks, it is necessary to carry out an IMS calibration test under the same conditions of the real analysis, with a water content in argon such that the RIP is not extinct. A complete spectrum is thus obtained. The presence of the RIP allows assignment of the other peaks to the corresponding species, this correspondence being maintained in the real analysis (without RIP).

EXAMPLE

The invention will be further explained by the following example, relating to a series of tests of water analysis with different concentrations in argon. In all the tests, the gas mixture flowing into the IMS instrument 10 is maintained equal to 0.5 liters per minute, and the gas temperature is 110° C. The sample ionization is carried out by a $^{63}Ni$ radioactive source. The ions so generated are neutralized onto grid 13 until the voltage of the latter is canceled, thereby allowing their entrance into the separation zone 12. The cancellation time of the grid voltage is 200 microseconds ($\mu s$) for each test. The tests are carried out with an IMS instrument 10 wherein the separation zone 12 is 8 cm long. In every test the acceleration electric field is equal to 128 V/cm. From preliminary calibration tests it is determined that under these conditions the typical drift times of the species present in the tests are generally between 15 and 30 milliseconds (ms). Moreover, with a suitable test it has been determined that under these conditions the peaks of $H_3O^+$ and $(H_2O)_2^+$ are between 15.5 and 17 ms and between 17 and 19 ms, respectively (with maximums at about 16 and 17.8 ms, respectively). The results of all the tests are reported in spectra 19 of the display and/or printer 18 (FIG. 1), wherein the peaks have an area proportional to the concentration of a given ion according to the drift time of the same. The peak intensity is expressed in volts (V), while the current directly measured by detector 14 (number of ions colliding onto the detector per unit time) is transformed in volts by converter 17. The counter-flow of pure argon coming from duct 16 has a rate of 2 liters per minute. Generally, the ratio between the flow rate of the gas to be analyzed and the counter-flow of pure argon can vary between 1:10 and 1:1.

Figure 2:
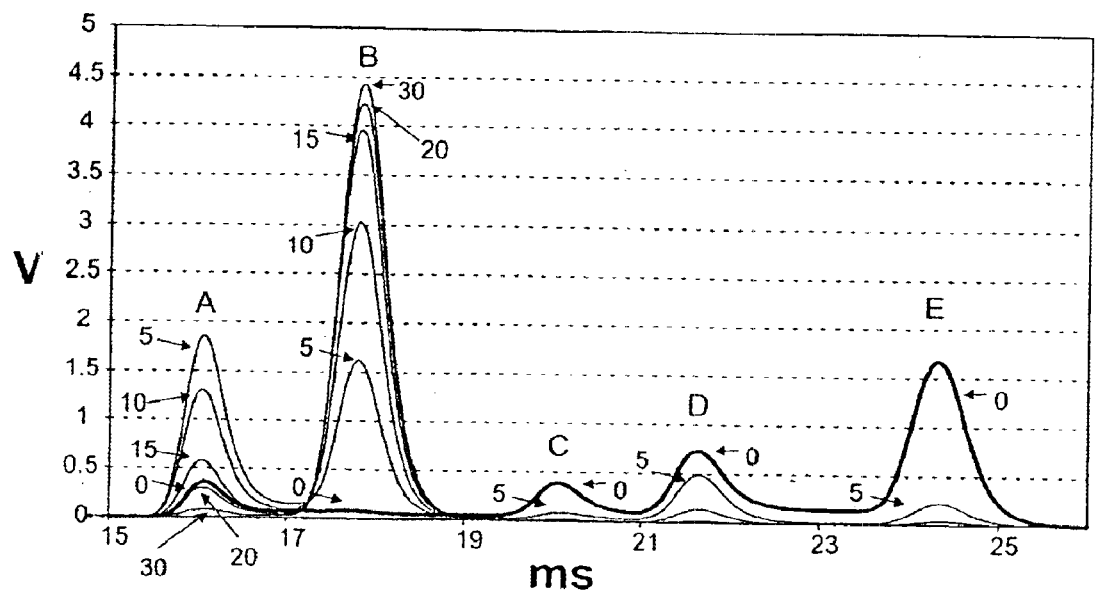
FIG. 2 is a graph showing some spectra obtained through the instrument of FIG. 1.

FIG. 2 shows a plurality of overlapping spectra obtained by analyzing with the IMS instrument 10 a corresponding plurality of mixtures of water, argon and very little impurities, wherein only the water concentration changes. Along the abscissa (x-axis) is shown the drift time of the ions in milliseconds, while along the ordinate (y-axis) is shown a value proportional to the intensity of the signal emitted by the ion detector 14, for instance a voltage expressed in volts. The numbers inside the diagram distinguish the different spectra according to the water concentration expressed in ppb present in the gas let into the IMS instrument 10.

As it can be seen, without the presence of water, i.e., with 0 ppb of water, the relevant spectrum (shown with a bold line) has 4 peaks A, C, D and E, the last of which is the tallest. The last peak E, which under the conditions of the present test is in the time interval between 23 and 25 ms, corresponds to the peak of the $Ar^+$ ions, i.e., to the RIP, while the other peaks A, C and D, in the time intervals between 15.5 ms and 17 ms, 19 and 21 ms, and 21 and 23 ms, respectively, correspond to the ions of the impurities present in the gas mixture. In particular, the peak in the first time interval A is caused by the ions of $H_3O^+$, the second peak C is caused by the ions of the impurities, and the third peak D by the ions of $H_2O^+$. The ions of $H_2O^+$ and $H_3O^+$ of peaks A and D are due to very small water concentrations which cannot be eliminated from the incoming gas mixture.

By increasing to 5 ppb the water concentration in the gas mixture and by keeping unchanged the other variables of the test, it can be seen how the heights of peaks C and E markedly fall, and the height of peak D is also slightly reduced, while the height of peak A grows. Further, in the time interval between 17 and 19 ms a new peak B which is caused by the $(H_2O)_2^+$ ions can be distinguished. At 5 ppb water, peaks A and B have heights similar to each other, and in any case higher than the remaining peaks C, D, and E.

By increasing the water concentration in the mixture from 5 ppb to about 30 ppb, the height of peak B grows, while the height of peak A falls and peaks C, D and E substantially disappear. In particular, at around 18 ppb of water the height of peak A is equal to the height of the same peak with 0 ppb of water.

By further increasing the water concentration in the mixture beyond 30 ppb, the system is saturated and only peak B remains with a constant height.

As the positions of peaks A and B were already previously determined with a calibrating test, thereby resulting in the time intervals between 15.5 and 17 ms and between 17 and 19 ms. By evaluating the intensity of these peaks, and in particular their area, the corresponding levels of the signal measured by the ion detector 14 are obtained. The water concentration contained in the analyzed gas can be determined by comparing the levels. In particular, for water concentrations lower than 30 ppb, it has been discovered that the comparison can be expressed with the following formula:

$$ppb_{H2O} = K \ln((HB+HA)/HA), \text{ wherein:}$$

$ppb_{H2O}$ is the water concentration,

K is a positive constant,

HA is the area of peak A, and

HB is the area of peak B.

Figure 3:
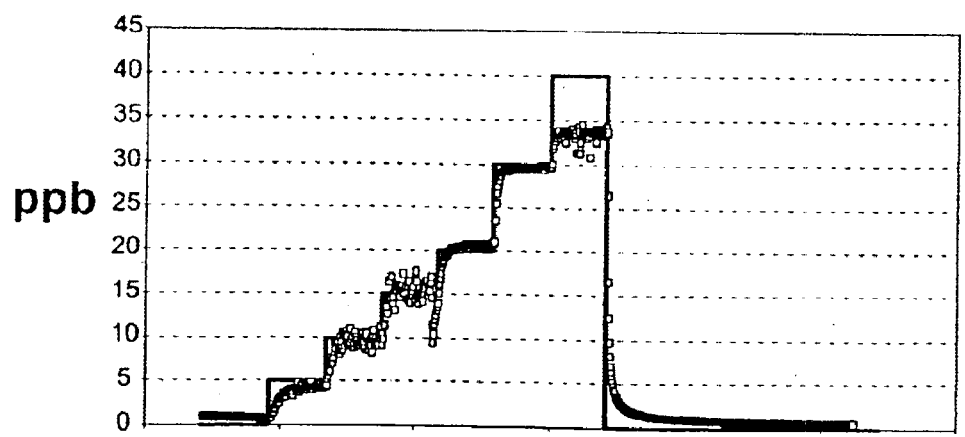
FIG. 3 is a graph of some test curves of the instrument of FIG. 1.

FIG. 3 is a graph showing the change over time (abscissa) of two overlapping curves of the water concentration (ordinate). The first curve, made up of a continuous stepped line, shows the water concentration effectively present in a reference mixture let into the IMS instrument 10, while the second curve, made up of a dotted line, shows the water concentrations measured by the above described method. As can be seen, the course of the second curve substantially follows the course of the first curve up to 30 ppb, while differing beyond this concentration at which the instrument is saturated.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for measuring a concentration of water in argon, hydrogen, nitrogen or helium by ionization mobility spectrometry (IMS), comprising the followings operative steps:

introducing a gas mixture to be analyzed comprising water and at least one selected from the group consisting of argon, hydrogen, nitrogen, and helium into an IMS instrument with a counter-flow of pure gas;

obtaining a signal variable over time and proportional to a number of ions detected by an ion detector of the IMS instrument;

determining two time intervals (A, B) corresponding to drift times in the IMS instrument of $H_3O^+$ and $(H_2O)_2^+$ ions present in the gas mixture;

obtaining peaks of the signal in the two determined time intervals (A, B); and calculating the water concentration in the gas mixture according to a ratio of intensity of the two peaks obtained in the signal.

2. The method according to claim 1, wherein the water concentration in the analyzed gas is calculated by the following formula:

$$ppb_{H2O} = K \ln((HB+HA)/HA), \text{ wherein:}$$

$ppb_{H2O}$ is the water concentration in ppb,

K is a positive constant,

HA is the intensity of the peak of the signal in the time interval (A) corresponding to the drift times of $H_3O^+$ ions in the IMS instrument; and HB is the intensity of the peak of the signal in the time interval (B) corresponding to the drift times of $(H_2O)_2^+$ ions in the IMS instrument.

3. The method according to claim 2, wherein areas of the peaks are employed as measures of the intensity of the respective peaks.

4. The method according to claim 2, wherein heights of the peaks are employed as measures of the intensity of the respective peaks.

5. The method according to claim 1, wherein the two time intervals (A, B) corresponding to the drift times of the $H_3O^+$ and $(H_2O)_2^+$ ions in the IMS instrument are determined with a preliminary calibrating test carried out with values of operative parameters equal to those employed in an actual analysis.

6. The method according to claim 5, wherein the operative parameters comprise at least a temperature of the analyzed gas mixture.

7. The method according to claim 6, wherein the operative parameters further comprise a ratio between an applied electric field and a gas pressure in a separation zone of the IMS instrument.

8. The method according to claim 5, wherein the analysis is carried out with gases at a temperature of 110° C. and with an electric field of 128 V/cm in a separation zone of the IMS instrument, and the two time intervals (A, B) corresponding to the drift times of the $H_3O^+$ and $(H_2O)_2^+$ ions in the IMS instrument are between 15.5 and 17 ms (A) and between 17 and 19 ms (B).

* * * * *